United States Patent [19]
Chodorow

[11] Patent Number: 5,922,000
[45] Date of Patent: Jul. 13, 1999

[54] LINEAR PUNCH

[75] Inventor: Ingram S. Chodorow, Upper Saddle River, N.J.

[73] Assignee: Redfield Corp., Montvale, N.J.

[21] Appl. No.: 08/974,484

[22] Filed: Nov. 19, 1997

[51] Int. Cl.⁶ .................................................. A61B 17/32
[52] U.S. Cl. ........................ 606/167; 606/184; 606/186; 606/187; 623/15; 600/567
[58] Field of Search .................................. 606/131, 132, 606/133, 183, 184, 185, 186, 187; 604/272; 600/562, 564, 566, 567, 568; 83/691; 623/15

[56] References Cited

U.S. PATENT DOCUMENTS

| | | | |
|---|---|---|---|
| 4,476,864 | 10/1984 | Tezel | 606/131 |
| 4,873,991 | 10/1989 | Skinner | 600/567 |
| 5,507,765 | 4/1996 | Mott | 606/184 |
| 5,766,177 | 6/1998 | Lucas-Dean et al. | 606/83 |
| 5,792,163 | 8/1998 | Hitzig | 606/167 |
| 5,792,169 | 8/1998 | Markman | 606/186 |

*Primary Examiner*—Michael Buiz
*Assistant Examiner*—David O. Reip
*Attorney, Agent, or Firm*—Ostrolenk, Faber, Gerb & Soffen, L.L.P.

[57] ABSTRACT

A hair transplant scalp punch comprising a handle and a plurality of punch elements extending from one end of said handle, each punch element having a proximal end secured to said handle and a distal end remote from said handle, each of said distal ends formed as a sharp cutting edge, each cutting edge having a elongate shape, said cutting edges being spaced apart from each other with their said elongate shapes each having opposite sides and opposite ends and being generally parallel to each other.

19 Claims, 10 Drawing Sheets

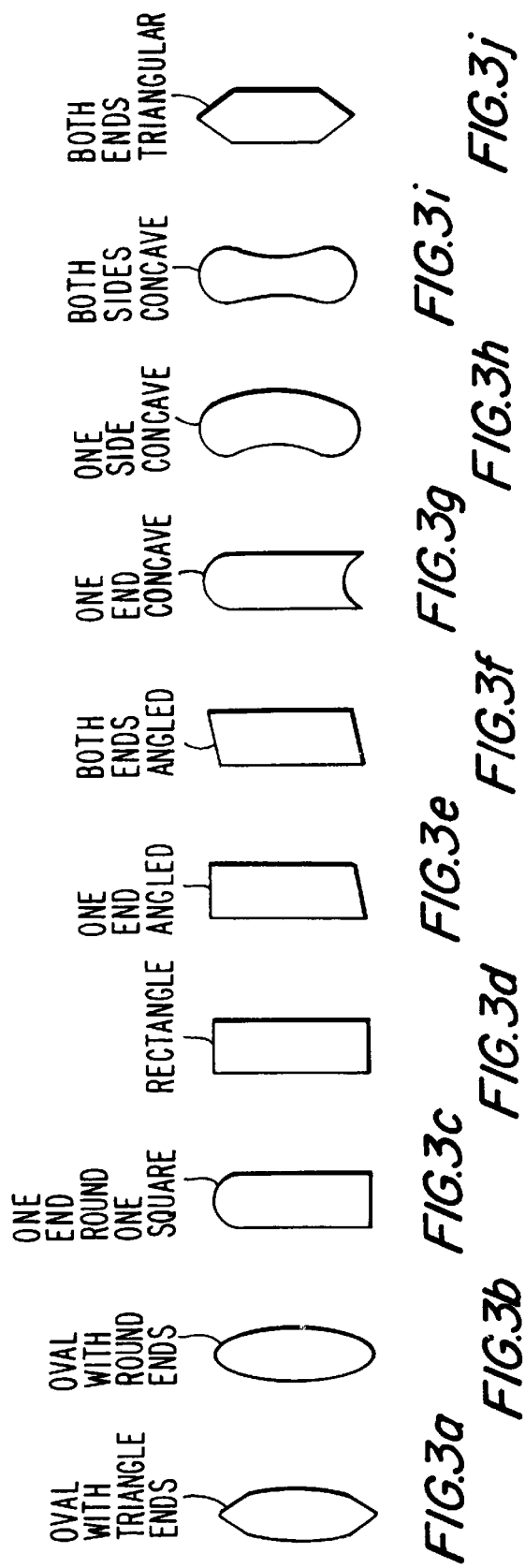

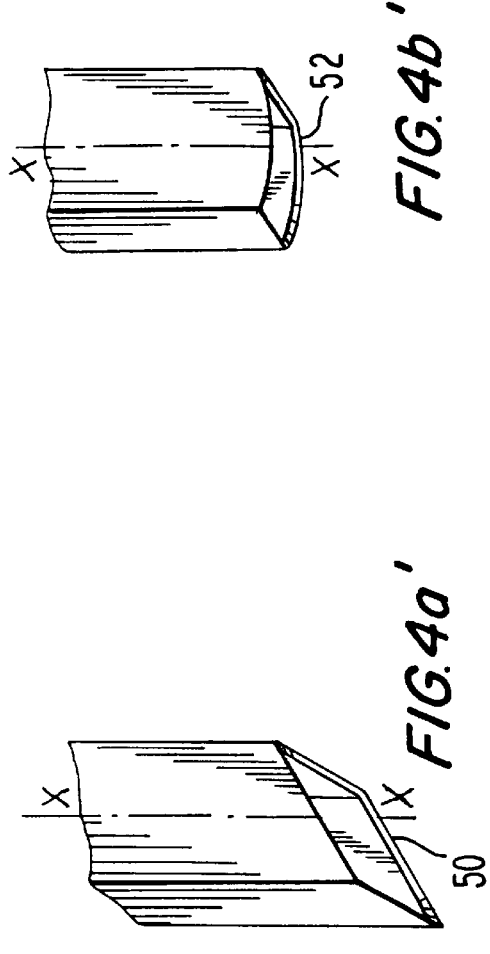
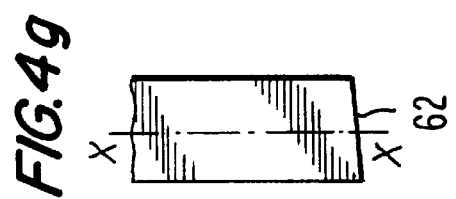
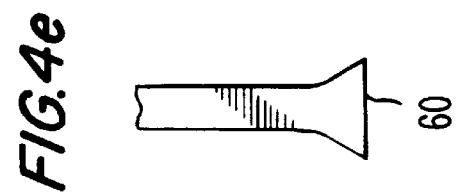
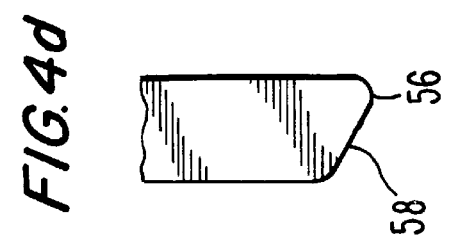
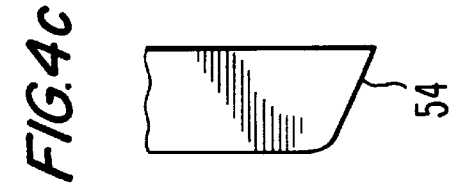
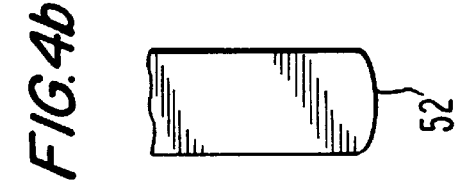
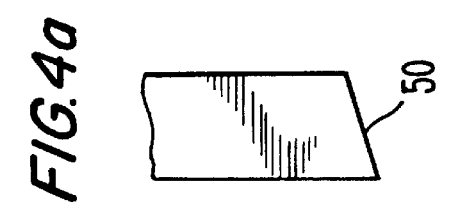

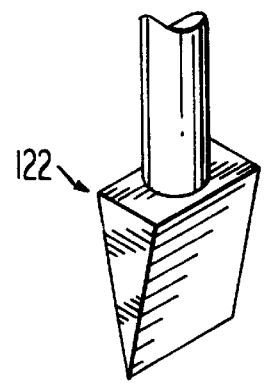
*FIG.12*
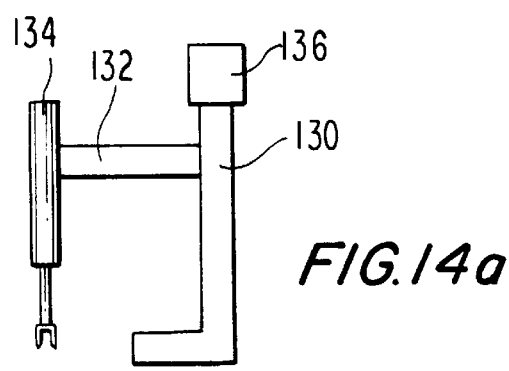
*FIG.14a*
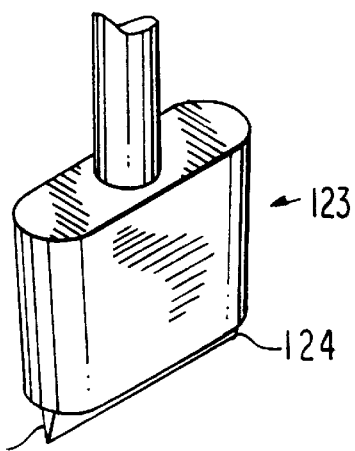
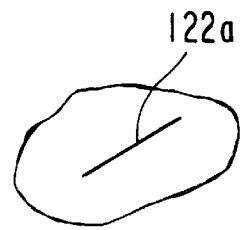
*FIG.13*
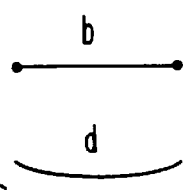
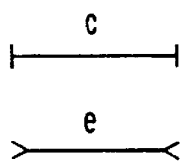

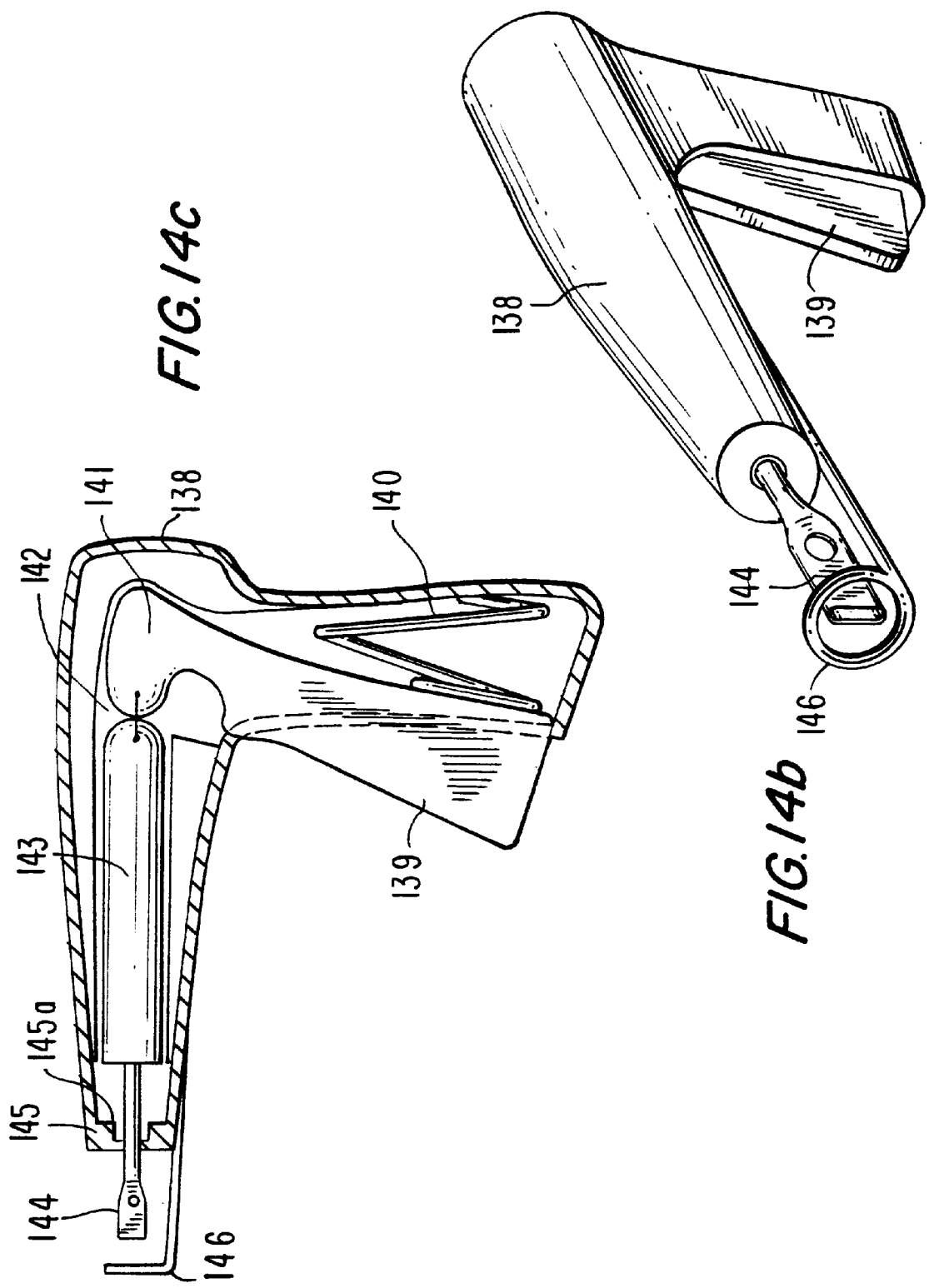

LINEAR PUNCH

FIELD OF THE INVENTION

This invention is in the field of surgical instruments for hair transplant and hair graft surgery, and particularly in the field of a disposal surgical punches for creating apertures in the scalp into which hair plugs or grafts are inserted.

BACKGROUND OF THE INVENTION

Male pattern baldness (MPB) affects more than 35 million men in the United States. It correlates closely with age whereby about thirty percent of men experience MPB by age thirty, forty percent by age forty and so on. For more than thirty years doctors have been refining the technique of harvesting a plurality of hairs from donor sites on the scalp and transplanting them to the areas of hair loss. It is not well known that hair loss is not associated with scalp location but with the particular type of hair follicle, which differs from site to site. Therefore, healthy follicles from a site where hair has not been lost will flourish when transplanted to a site where hair had been lost.

Early attempts at transplantation involved removing of circular plugs of hair from a donor site and inserting them into circular recipient holes in another site. Surgeons now remove long rectangular sections of scalp from the donor site which is then closed by suturing or stapling the remaining parallel cut edges of scalp together. This leaves a long, straight mild scar, which is not visible when it becomes covered by hair. The donor tissue is then cut into sections, each containing one or more hair follicles, in sizes that will match the size and shape of the recipient sites.

In order to avoid the unattractive "corn row" appearance, most surgeons prefer to implant narrow rectangular sections of donor tissue or donor grafts so that the normal pattern of hair growth can be approximated. The recipient sites have generally been created by making slits with a scalpel or laser. These methods have not been fully successful, because the mass of the tissue plug is greater than the slit that has been created for it. The result is often graft compression which causes a clumpy appearance. Optimal blood flow is not achieved and healing is compromised, resulting in incomplete survival of the donor hair follicles. If the grafts are pushed upward during healing, a series of bumps or ripples in the scalp will result.

The use of circular scalp punches of varying sizes involved puncturing the scalp with the sharpened circular tip of the punch to a depth of several millimeters and then removing the circular tissue plugs. These punches are essentially hollow tubes, sharpened at one end, with one or more relief holes to allow blood and tissue an escape path after the holes have been made. The circular punch was initially selected because it was an obvious cutting tool with a history of use in securing tissue biopsies. It was also readily available, inexpensive and easy to use. It made a clean, round circular cut and could be matched in size to the diameter of the donor graft.

Hair transplant plugs have to be made or harvested from other portions of the scalp where there is a healthy growth of hair. An area approximately three quarters of an inch by five inches, for example, is usually removed from the back of the head. The edges are parallel top and bottom and the sides taper to points so that the edges can be brought together to form a straight suture line. The slab of skin which includes hundreds to several thousand hair follicles is then sliced longitudinally and horizontally to produce the individual plugs each having from one to five or more hair follicles. By this method each donor plug is essentially a rectangle in shape or a square. When placed into a round opening which has been prepared to receive the transplant a good fit is not always achieved because of the disparity between their shapes. While the plug is very soft and may tend to conform its rectangular shape and straight sides to a circular hole, it clearly is not a mating fit.

It was discovered over a period of time that a pattern of round holes creates an unnatural look as regards the appearance of hair in a person's scalp. Normal hair does not grow in round sites or in a pattern of such sites.

A relatively new development to improve on these problems is a device called the linear punch which is a punch having a generally rectangular shape as opposed to round. The result is that hair plugs of a rectangular shape fit more appropriately into a generally rectangular shape hole, and furthermore the transplant plugs being essentially linear create the impression of lines of hairs as opposed to round spots. When these lines are properly located in an appropriate pattern, the eventual hair growth has a more much natural look because the extended hair will grow and overlap spaces between adjacent lines and the result is cosmetically desirable and superior.

The linear punch referred to above has parallel sides and round or semicircular ends. This punch is formed as a hollow tube, typically round along its stem until reaching the cutting end which is then partially flattened to create the above-mentioned parallel sides and rounded ends. This punch produces a generally rectangular opening for receiving a generally rectangular transplant hair plug. This linear punch is secured to a handle, and the surgeon makes a great many manually punched holes in the scalp. The spacing and pattern of the holes and the depth of each hole is determined essentially by the surgeon's skill, experience and aesthetic decision about the scalp surface being punched.

In the punching procedure each time a penetration of the scalp is made and the surface is cut to the determined depth, a small bit of tissue is forced up into the opening of the punch bore. After a plurality of punch strokes some tissue and blood can travel upward through the hollow bore of the punch and exit through a relief hole in an upper portion of the stem of the punch. Sometimes after the punch is withdrawn from a site, the cut tissue either remains in the site or stays in the punch. The surgeon removes dangling tissue on the scalp by wiping the surface with a comb or cloth or by other methods such as grasping forceps and removed tissue from the punch by shaking it.

The surgical technique used with the above-mentioned linear punch and the punch itself constitutes a considerable improvement over prior methods and devices and in the health and cosmetic appearance of the hair transplant result.

SUMMARY OF THE INVENTION

The present invention takes its starting point with the technique and device of the linear punch described above and proceeds to make substantial improvements thereon. The improvements are in a number of areas including the shape of the punch at the cutting surface and in an arrangement of a plurality of punches on a single handle which may be manually or motor driven. It has been determined that it is unnecessary to have a punch cutter surface having parallel sides and rounded ends of the prior art. In fact, in some cases it would be preferable to have a more rectangular shape to conform to that of rectangular plugs. Also, the cutting edge shape could comprise an oval or generally rectangular shape with ends tapered to a generally triangular shape.

Another significant advance of the new invention over the known linear punch is the provision of a multiple tip punch which has two, three or other plurality of punches fixed in a specified pattern on the end of the handle. This provides a variety of advantages over the prior art single punch device. With the multiple tips the spacing between sites will be automatically established as between those tips. Thus, the resulting spacing and pattern is not solely a consequence of the surgeon's ability to estimate distances and positions. Also, the surgeon will create multiple sites with each punch stroke which will be less work for him or her and achieve the result in less time. This is a significant factor when one considers that the surgeon may make hundreds of punches in a patient's scalp during one surgical procedure.

When using the multiple tip concept the pattern of tips on a single handle could be linear in the sense that two or more tips or cutting edges are aligned, or they may be arranged in other patterns of choice. The result ultimately will be a pattern of hair transplants which when matured will provide the most cosmetically pleasing and natural look. One preferred pattern is to position the tips with two side-by-side and a third parallel but displaced downward, so that the three create a generally triangular appearance, but in fact produce three linear or mutually parallel rectangular cuts.

Another feature of the new punch is an upward extending barb extending inwardly from the inner bore surface and located near the cutting edge. When a punch of this type is used and the cutting surface penetrates the skin and the cut tissue is caused to rise into the bore of the punch, the barb would engage that tissue such that upon withdrawal of the punch the barb would ensure that the cut tissue would rise out of the site. This eliminates the problem of the surgeon having to go back and waste time removing such portions of tissue. It also eliminates a most unaesthetic aspect of dangling pieces of bloody tissue on the scalp.

The method of manufacturing the new punch or multi-tip punch is generally as follows. A steel tube of round diameter is selected or is created by boring a circular hole in a solid circular rod. Next a rectangular solid form is placed within the bore of the tube and a compression device smashes or otherwise forces opposite sides of the tube toward each other upon the form inside, thus establishing the generally parallel sides or other shapes as desired. The ends of the rectangular shape of the tube may be perpendicular to the sides thus producing a rectangle, or these ends may be tapered.

The exposed end edges of this tube become the cutting surface. These edges are sharpened either by creating a bevel on their inner surface or outer surface or on both surfaces. Because of the very small size of this punch and particularly of the punch opening, it is preferable and easier when sharpening the cutting edge to bevel the exposed outer surfaces of this edge; however, to bevel the outer side is an option. A technique for beveling and sharpening the inside and outside cutting edges of this tool is to use a conical shaped grinding wheel with its pointed end directed into the opening of the cutting end of the punch. The grinding wheel is then moved laterally along the side edges and end edges of the punch until all surfaces are beveled on the inside surface. The same conical shape grinding wheel could be used to bevel the outside edges by moving it laterally thereon, or both inside and outside edges could be ground.

It is imperative that the cutting edges be extremely sharp and extremely strong, because the surgeon will be using the instrument very rapidly and repeatedly a great number of times (in the hundreds). Each punching cut must be quick and clean to be successful both from the patient's point of view and from the doctor's point of view. To achieve such strength and sharpness and to have a cutting edge that will retain both strength and sharpness during these procedures, the punch is made of stainless steel which is hardened after sharpening.

It is contemplated that a multi-tip punch or even a single tip punch be coupled with an automatic drive means which is held by the surgeon and which is positioned and braced on the scalp such that the cutting edge of the punch or punches descend and penetrate the scalp to a predetermined and correct depth and eliminate the need for physical strength of the surgeon and accuracy of depth by the surgeon. Obviously a surgeon's hands and arms become somewhat fatigued after making dozens or hundreds of punches; also his ability to create sites of uniform depth and spacing will be impaired over a period of time. An automatic and/or power driven device will overcome these problems. Power may be provided by an electric or hydraulic motor, mechanical spring or $CO_2$ cartridge.

A further new feature and alternative to the earlier described upward barb in the punch of the present invention for dealing with the problem of tissue not coming out of the scalp when the punch is withdrawn, is to apply a suction through the handle to the top end of the hollow punch bore.

A still further variation on the new linear graft concept is to achieve a pattern of generally linear sites by a cutting tool comprised of two parts namely a pair of generally straight parallel spaced apart blades to create a pair of parallel spaced cuts for the sides of the rectangular cut site and a second pair of blades which may be straight or curved to create the end cuts of the rectangular site. These pairs of cuts would be created sequentially by a single device in which one set of blades is spring loaded with respect to the others. Subsequently, the tissue from the cut site is removed. A punch device of this type could alternatively have the number of parallel blades increased from two to three, four or more which would allow the surgeon with a single stroke to make a plurality of cuts which are automatically spaced apart the proper distance from each other. As discussed above, this would eliminate the need for estimating by the surgeon and would also provide a more accurate and attractive hair pattern even though the surgeon might tire during the long surgical procedure.

A variation on the above multi-blade linear punch is to have a discontinuation in the cutting edge of each blade, thus producing a pair of cutting edge segments. Then, each time the punch is applied to the scalp surface, each blade will create two spaced apart cuts as opposed to one, and therefore the surgeon will achieve automatically additional spaced cuts without having to make more thrusts with the punch tool.

The punch when manufactured from a round circular tube may retain that shape with its distal end sharpened into a round cutting edge, or the distal end may be partially flattened to a rectangular, oval or other shape, or the tube may be partially flattened along its full length. When the proximal end remains round such end is generally more suitable for mating with a round element of the handle.

When viewing the cutting edge from the side as opposed to the open end, the cutting edge may be perpendicular to the vertical axis of the punch or may be tapered with respect to said axis or curved. These different shapes may be selected for different attack modes in the intended surgical procedure, depending upon the shape and characteristics and condition of the scalp and depending upon the location of the sites with respect to the shape of the scalp.

A still further new form of punch makes a slit for insertion of a graft without removing tissue as with the open hollow punches. This variation comprises a blade and dilator whereby the blade is thin and sharp and tapers outwardly to be thicker at its upper part remote from the cutting edge. As the punch is inserted and moved to its full depth, it forces the slit opening to become wider. A variation on this provides an additional cutter at the upper portion of the blade, upward of the bottom principal cutting edge. After the slit is made and dilated and the punch has descended into the slit, a very tiny traverse cut is made at each end of the slit by the elevated cutter edge. The result is that when the graft is inserted into the slit opening, it is easier to spread the sides of the slits apart because their ends are cut transversely. Such a slit punch may be formed as a very simple triangular wedge which would produce a straight slit, or it could be formed somewhat oval in cross section but still tapering to becoming wider in the upward direction from the cut edge.

Lastly, is the feature of relief holes in the upper portion of the punch. As previously discussed, as the punch is repeatedly used blood and/or tissue rises in the bore and there must be "relief" or opening for this fluid and tissue to be ejected readily. The relief holes must be adequate for the stated purpose but not so large as to weaken the tubular punch.

It is contemplated that the various punches described above will be fixedly secured on a handle, and the entire device will be disposable either when the procedure is finished, or earlier if the surgeon decides that the cutting edges are no longer sharp enough. A handle for this punch would preferably be made of injection molded plastic, and the metal punch would be secured in one end of the handle by any of a variety of well known means. The handle may be of a generally cylindrical shape and may have indentations for easy or better gripping by the physician's fingers and hands, or the handle may have a type of pistol grip for secure engagement and minimum of physical strain in use.

The drawings illustrate various embodiments of the invention which will now be described in further detail.

BRIEF DESCRIPTION OF THE DRAWINGS

FIGS. 3a–3j show bottom plan views of various punch cutting edges.

FIGS. 4a, 4a', 4b, 4b', 4c, 4d, 4e, 4f and 4g show various tip angles and shapes of the punch.

FIGS. 12 and 13 show various slit graft plus dilator punches.

FIG. 14a shows schematically a power drive mechanism for the punch.

FIG. 14b is a perspective view of a power drive device.

FIG. 14c is a sectional view of the device of FIG. 14b.

DESCRIPTION OF THE PREFERRED EMBODIMENTS

Figure 1:
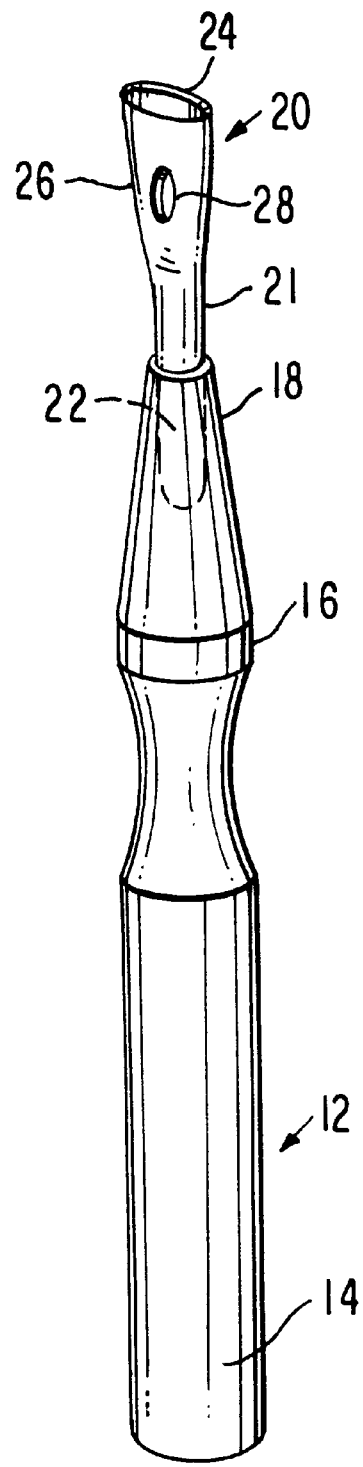
FIG. 1 shows a perspective view of the new punch and handle combination.

The basic linear punch 10 is shown in FIG. 1 including a handle 12, having a proximal end 14, a distal end 16 terminating in a punch-engaging portion 18, and a punch 20 having a central body 21 with a handle-engaging portion 22, a cutting edge 24 at the distal end thereof, a transition area 26 and a relief aperture 28. Area 16 may have a variety of contours for comfortable and secure gripping by the surgeon. The punch 20, which will be described in much greater detail below, is preferably attached permanently to the handle 12, the resulting surgical instrument being totally disposable.

The punch portion of this instrument may have a great variety of cutting edge forms and combinations, as exemplified but not limited by FIGS. 2a–2d. The first punch variation 30 shown in FIG. 2a has a pair of aligned punch elements 32a, 32b secured to the body part 34. The alignment of these punches is within a common plane defined by the x-y axes seen in FIG. 2a.

Use of this punch produces a pair of aligned and slightly spaced apart holes or sites in the scalp corresponding to the shape, size and orientation of these two punches. Thus, with a single punch stroke, the surgeon produces a pair of sites with an exactly predetermined shape and spacing. To produce a pair of sites with each stroke reduces the time and effort required by the surgeon and the time spent by the patient in surgery, and also helps the surgeon produce accurately spaced sites and better esthetic results.

Figure 2A:
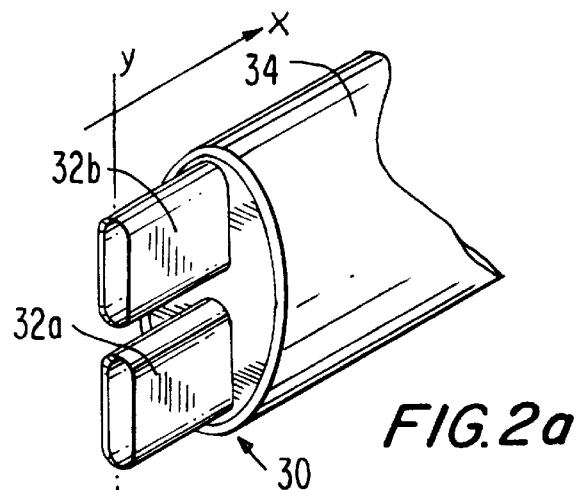
FIGS. 2a, 2b and 2c show perspective views of multiple tip punches respectively of 2, 3 and 4 tips.
Figure 2B:
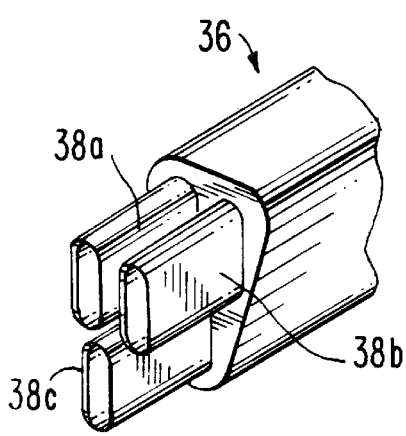

FIG. 2b shows a second embodiment of a multiple-head punch 36 having three aligned punches 38a, 38b and 38c arranged with punches 38a, 38b parallel and adjacent and the third punch 38c situated below and between the upper two punches forming a generally triangular arrangement. This multiple-tip punch also produces a pattern of linear sites which can be conveniently repeated in adjacent or overlying locations to produce the desired overall pattern on the scalp.

Figure 2C:
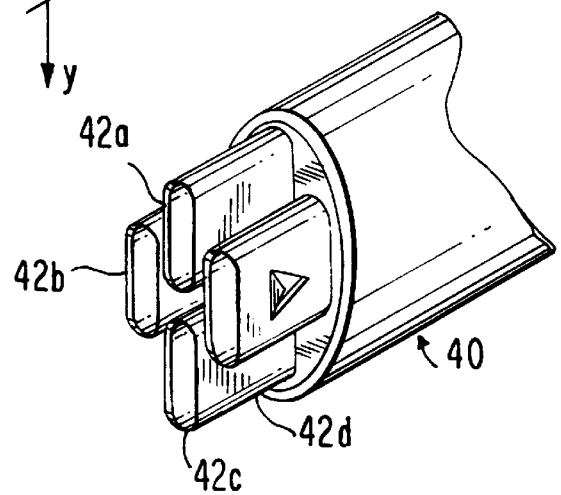
Figure 2D:
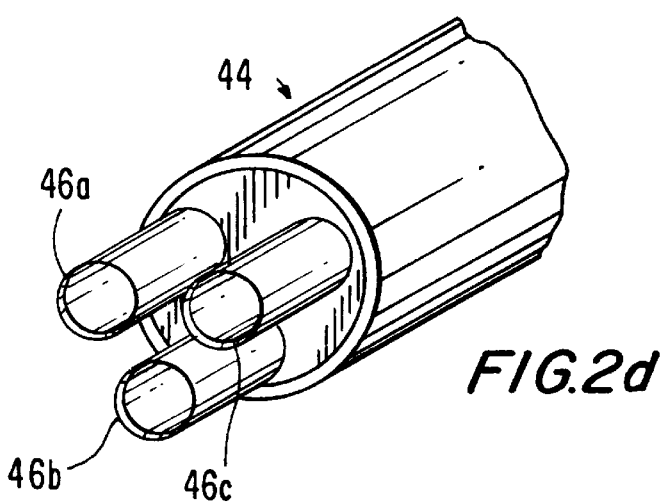
FIG. 2d shows a similar view of another punch.

FIG. 2c shows a still further variation 40 of a multiple punch with a set of four punch tips 42a–42d arranged in parallel and overlying relationship. More specifically, tip 42b overlies the space between the tips 42a and 42c. This arrangement or pattern of sites is intended to enhance the appearance of later hair growth and distribution. As with the multiple-tip punch of FIGS. 2a and 2b, this punch 40 automatically provides a predetermined correct spacing, shape and orientation of the sites. FIG. 2d shows still another punch variation 44 of three tips 46a, 46b, 46c where one resulting site always overlaps or overlies the space between the adjacent two spaced sites.

FIGS. 3a–3j illustrate various shapes of punch cutting edges corresponding generally to cutting edge 24 in FIG. 1. These punch shapes obviously produce sites in the scalp of the shape and size as selected by the surgeon. Described briefly, FIG. 3a is an oval with triangular ends; FIG. 3b is an oval with round ends; FIG. 3c is generally rectangular with one square end and one rounded end; FIG. 3d is a rectangle; FIG. 3e is generally rectangular with one square end and one angled end; FIG. 3f is generally rectangular with two angled ends; FIG. 3g is generally rectangular with one convex end and one concave end; FIG. 3h is generally crescent with opposite concave and convex sides; FIG. 3*i* has a pair of concave sides; and FIG. 3*j* is generally rectangular with triangular ends.

The cutting edge of the punches may vary in angle relative to the longitudinal axis. For example, in FIG. 1, the cutting edge 24 is perpendicular to longitudinal axis x—x. FIGS. 2*a*–2*d* also show perpendicular cutting edges; however, FIGS. 4*a*–4*g* show alternate cutting edges with different angles of attack and different profiles as seen from the long side of the linear punch. FIGS. 4*a* and 4*a'*, for example, have inclined edge 50; FIGS. 4*b* and 4*b'* have curved rocker edge 52; FIG. 4*c* has a sharper incline edge 54 than edge 50, and FIG. 4*d* has a rounded end 56 on its incline edge 58. FIG. 4*f* has a straight (perpendicular) but outward flared edge 60, and FIG. 4*g* shows the simple straight edge 62 perpendicular to its longitudinal axis x—x.

Figure 5A:
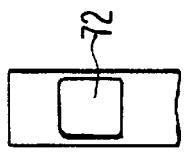
FIGS. 5a–5e show various relief hole shapes in the side wall of a punch.
Figure 5B:
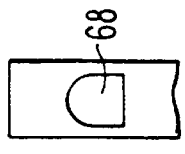
Figure 5C:
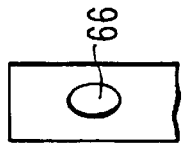
Figures 5D, 5E:
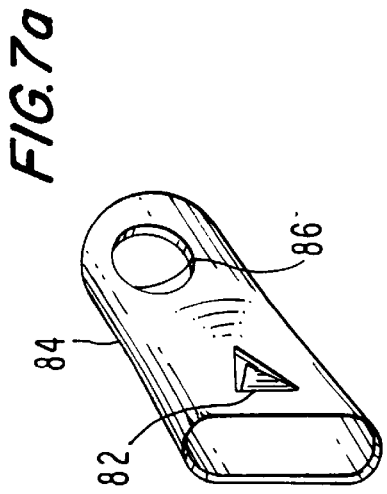

The relief hole 28 in FIG. 1 may take various forms as exemplified in FIGS. 5*a*–5*e*. This relief hole spaced from the cutting edge allows discharge of tissue, hair, blood and other fluid so that the punch will not become quickly clogged and unusable, as successive punch strokes are made. FIG. 5*a* shows a simple round hole 64 in a side wall of the stem or body 65 of the punch. FIG. 5*b* shows an oval 66, FIGS. 5*c* and 5*d* show opposite half-ovals 68, 70, and FIG. 5*e* shows a major aperture 72.

Figure 6A:
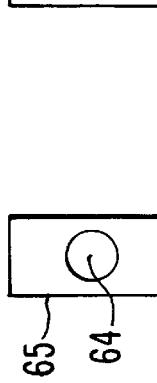
FIGS. 6a–6c show various shapes of punch.
Figure 6B:
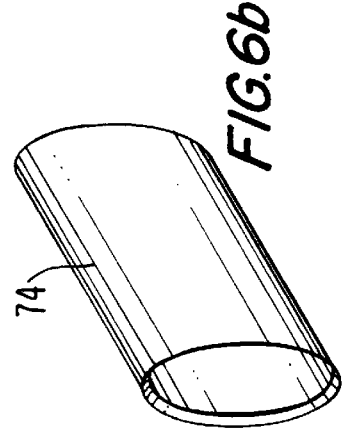
Figure 6C:
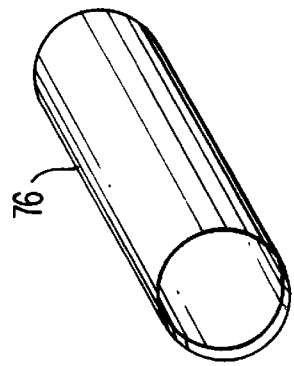

The oval cutting edge with round ends shown in FIG. 3*b* may be formed on a tubular stem of similar cross-section along its length as seen in punch 74 in FIG. 6*b*. Similarly, the round cutting edge 46*a* as seen in FIG. 2*d* may be formed on a round cylindrical tube as seen in punch 76 in FIG. 6*a*. FIG. 6*c* shows a fluted punch 78 with a round end 79 for attachment to a handle and an oval end 80 to serve as the cutting edge.

Figure 7A:
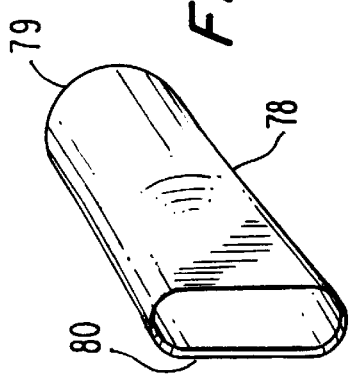
FIGS. 7a and 7b show various punches, each with a barb included in the wall surface.
Figure 7B:
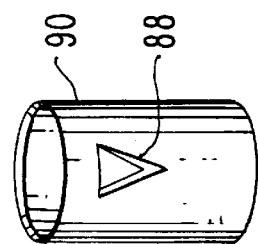

When a punch stroke is made into the scalp tissue rises into the stem of the punch inward of the cutting edge. Upon withdrawal of the punch out of the new site there may be a tendency of the cut tissue to descend out of the punch and remain in the scalp. To reduce such tendency, an upward pointing barb or hook 82 is provided in the punch embodiment 84 in FIG. 7*a* to engage and retain the tissue. Because of the barb's upward orientation successive tissue elements can continue to rise in the stem toward the relief hole 86 and cannot return toward the cutting edge. FIG. 7*b* shows a similar barb 88 in a circular punch 90 as contrasted with the fluted punch 84 of FIG. 7*a*.

Figure 8C:
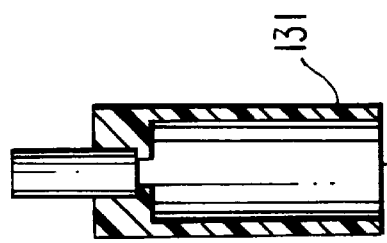
FIGS. 8a–8c show various handle and punch combinations.
Figure 8B:
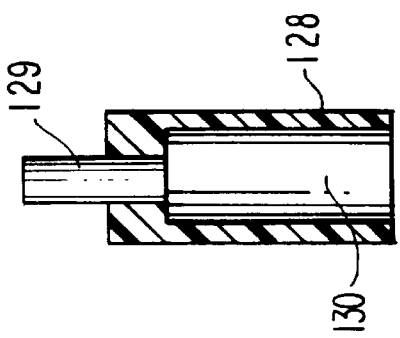
Figure 8A:
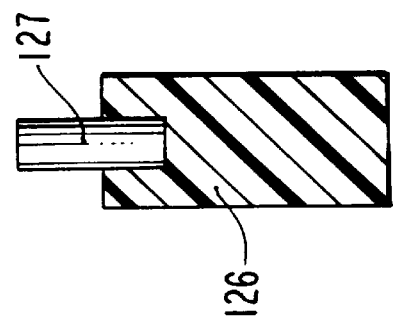

FIGS. 8*a*–8*c* show handle variations. In FIG. 8*a* there is a solid injection molded handle 126 and element 127 secured thereto which is either a punch stem or a connector for receiving and holding a punch stem. FIG. 8*b* shows a hollow handle 128 with punch or connector 129 secured thereto and a chamber 130 defined in the handle. FIG. 8*c* shows a hollow handle 131 adapted to be connected to suction means to apply suction through the punch to the punch site and to the tissue and fluid cut by the punch stroke.

Punches of the type described above can be made in a number of ways. A cylinder punch 46*a* of FIG. 2*d* or 76 of FIG. 6*a* can be made by starting with a cylindrical tube or by starting with a solid cylindrical rod whose outside surface is ground to create a perfect cylindrical edge and whose center is bored out to produce the cylindrical tube, and the vent or relief hole is cut. The cutting edge is shaped and sharpened and hardened, and the opposite end is adapted to engage a handle. For punches having cutting edges like those of FIGS. 3*a*–3*j* a solid form is inserted in the bore of the tube and the outer surface of the tube is forced and molded to the shape of the form. Punches of this type made of stainless steel are heat treated to about 49–52 Rockwell hardness, followed by chemical grinding of the cutting edge and press punch into a DELRIN® plastic handle. The punch 78 of FIG. 6*c* is initially a cylindrical tube which has one end flared or fluted into an oval shaped cutting edge.

Figure 9:
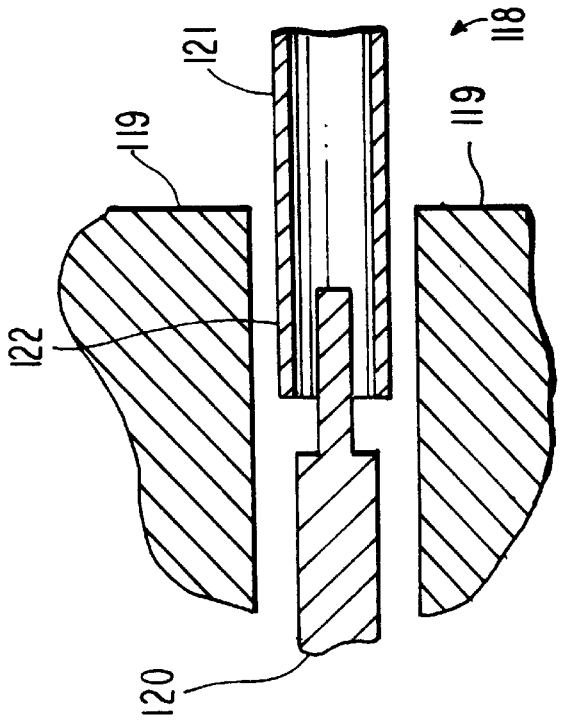
FIG. 9 shows an apparatus for forming the linear punch of FIG. 1.

FIG. 9 shows a forming apparatus 118 including former or compression means 119, an anvil or internal generally rectangular form 120, and the punch body part or stem 121. The distal end 122 of the stem is formed from round to oval or other desired shape as determined by the anvil shape and by selected contours that may be applied to the formers.

Figure 10C:
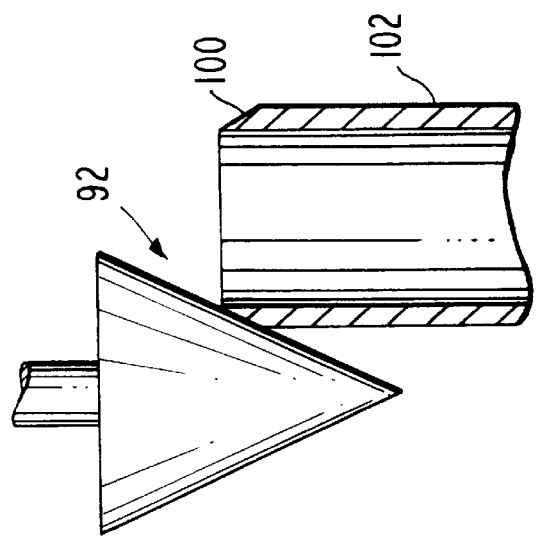
FIGS. 10a–10c show the method of sharpening the punch on the inside and outside edges.
Figure 10B:
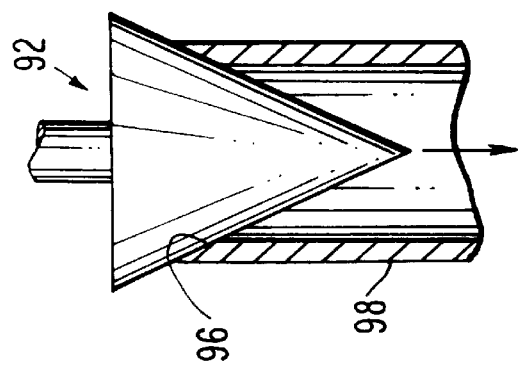
Figure 10A:
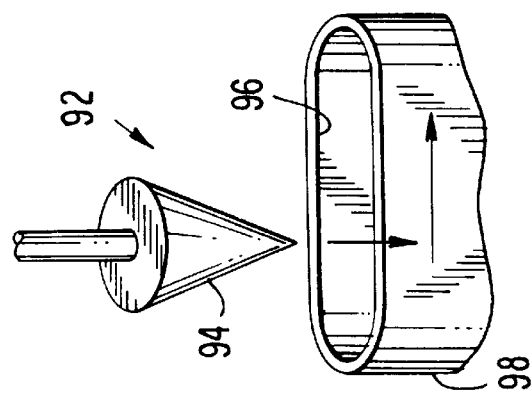

FIGS. 10*a*–10*c* show a sharpening apparatus comprising a conical grinding wheel 92 whose inclined grinding surface 94 can grind a tapered cutting edge 96 on the inner surface of a punch as seen on the oval punch 98 in FIGS. 10*a* and 10*b*. Alternatively, grinding wheel 92 can grind an external tapered cutting edge 100 on a punch 102 as seen in FIG. 10*c*. Obviously, the grinding wheel is manipulated to the required axial depth and then moved transversely along the cutting edge to achieve the desired taper and sharpness.

Figure 11A:
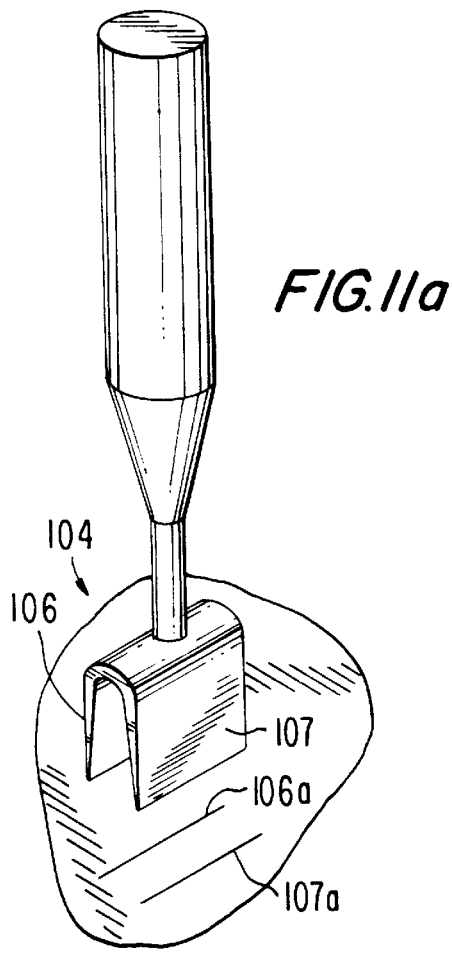
FIGS. 11a–11c show various multiple-blade linear punches and corresponding cut patterns.
Figure 11B:
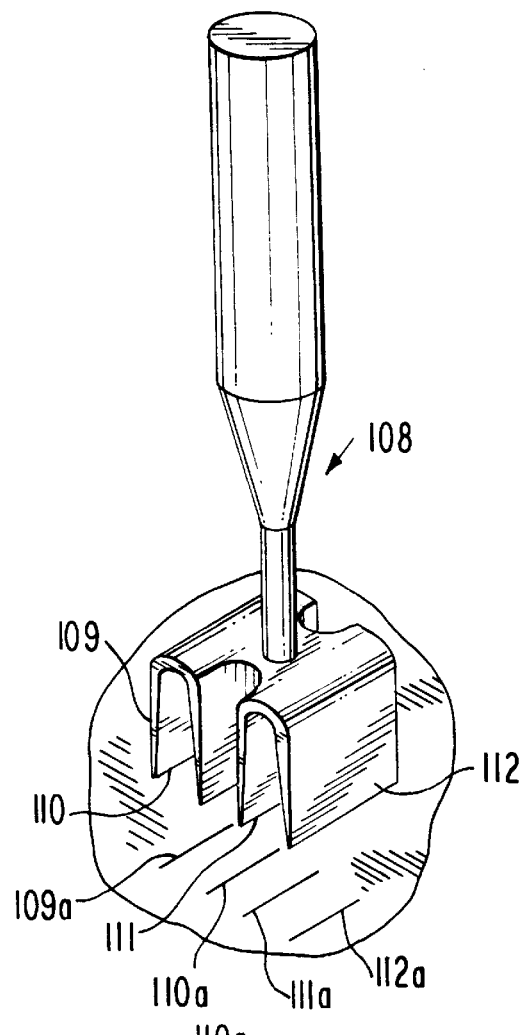
Figure 11C:
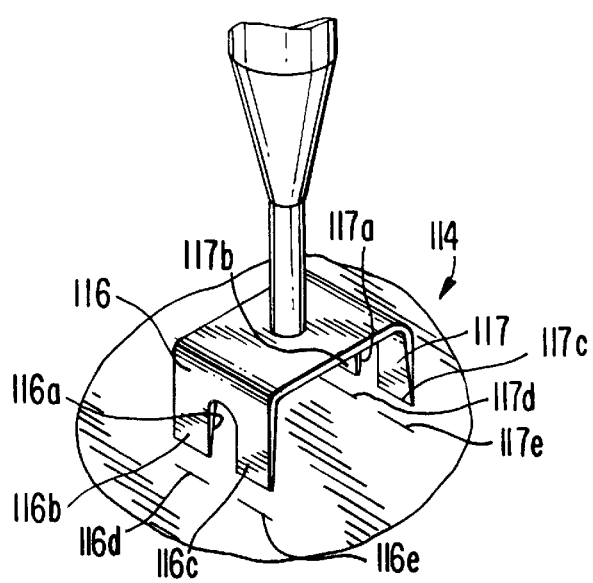

Additional embodiments of the present invention include bi-linear punches formed of a plurality of parallel blades to create multiple pre-aligned cuts with each punch stroke. FIG. 11*a* shows punch 104 with a pair of parallel and adjacent blades 106, 107 that produce a pair of corresponding cuts 106*a*, 107*a*. FIG. 11*b* shows a punch 108 having two pairs of parallel and adjacent blades 109, 110 and 111, 112 that produce two sets of cuts 109*a*, 110*a* and 111*a*, 112*a*. These blades may be formed or fabricated using conventional means and materials. A still further variation is seen in FIG. 11*c* where for punch 114 each of the parallel blades 116, 117 has a notch or discontinuity 116*a*, 117*a*. This produces cutting edge segments 116*b* and 116*c* and 117*b* and 117*c* for example which produce a set of four cuts 116*d*, 116*e*, 117*d* and 117*e* from a single punch stroke. The concepts inherent in the punches of FIGS. 11*a*–11*c* may be varied and combined in various ways.

A further variation on the punch form is the dilator seen in FIGS. 12, 13. The dilator type punch 122 is a generally triangular wedge that produces a simple cut or slit 122*a*. Dialator punch 123 is a contoured wedge comprising a blade 124 to produce a slit plus auxiliary cutting edge 125 to produce transverse or shaped ends of the slit as seen in FIGS. 13*b*–*f*. Slit 13*d* requires blade 124 to be curved.

For any of the punch embodiments disclosed above power drive means is contemplated, as seen schematically in FIGS. 14*a*–14*c*, for engaging and urging the punch element axially downward to make incisions of predetermined depth in the range of 2 mm to 5 mm in a patient's scalp, said power drive means in FIG. 14*a* comprising a housing 130, an axially reciprocating carrier element 132 for holding and axially reciprocating said punch element 134, and means 136 for driving said carrier element in said axially reciprocating motion. In FIGS. 14*b* and 14*c* there is housing or body 138, trigger 139, trigger spring 140, hammer 141, coupling 142, punch carrier or handle 143, and punch 144. Also this device has stop 145 and guide 146.

In the device of FIGS. 14*b*–14*c* the trigger 139 is pulled against its return spring 140 causing hammer 141 to pivot forward and drive the proximal end of the punch handle 143. The punch handle moves axially, driving the punch through guide 146; however, stop 145 has a shoulder 145*a* that prevents excessive axial movement of the punch. Spring 140 returns the trigger to its set position for another incision, and coupling 142 returns or withdraws the punch as the trigger returns. Electrical, hydraulic, $CO_2$ or other means may be used for the power source with known reciprocating mechanisms.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A hair transplant scalp punch comprising a handle and a plurality of punch elements extending from one end of said handle, each punch element having a proximal end secured to said handle and a distal end remote from said handle, each of said distal ends having a hollow tubular shape terminating as a sharp cutting edge, each cutting edge having an elongate shape, said cutting edges being spaced apart from each other with their said elongate shapes each having opposite sides and opposite ends and being generally parallel to each other.

2. Apparatus according to claim 1 wherein each of said elongate shapes is generally rectangular.

3. Apparatus according to claim 2, wherein said plurality comprises a pair and wherein said ends of said rectangular shapes are aligned with and adjacent to each other.

4. Apparatus according to claim 3 further comprising a third punch element similar to said pair of punch elements, with a side of said cutting edge of said third punch element adjacent and spaced from the sides of the cutting edges of said pair of punch elements.

5. Apparatus according to claim 4 wherein said cutting edge of said third punch element overlies the space between the cutting edges of said pair of punch elements.

6. Apparatus according to claim 2, wherein said plurality comprises a pair and wherein said sides of said rectangular shapes are aligned with and adjacent to each other.

7. Apparatus according to claim 6 further comprising a third punch element similar to said pair of punch elements, with an end of said cutting edge of said third punch element adjacent and spaced from the ends of the cutting edges of said pair of punch elements.

8. Apparatus according to claim 7 wherein the cutting edges of said three punch elements define a generally triangular configuration.

9. Apparatus according to claim 1 wherein each of said punch elements is a tube having a round cross-section at its proximal end.

10. Apparatus according to claim 1 further comprising power drive means for engaging the punch and for urging the punch element axially downward to make incisions of a predetermined depth in a patient's scalp, said power drive means comprising a housing, an axially reciprocating carrier element for holding and axially reciprocation said punch element, and means for driving said carrier element in said axially reciprocating motion.

11. A hair transplant scalp punch comprising a handle and a plurality of punch elements, each punch element comprising a tube having a proximal end secured to the handle and an opposite distal end which terminates in a sharp cutting edge, each of said cutting edges having a generally elongated shape, said plurality of punch elements situated parallel to and spaced apart from each other.

12. Apparatus according to claim 11 wherein each of said tubes defines a straight round cylinder with a central longitudinal axis, and said axes of said tubes are generally parallel.

13. Apparatus according to claim 12 wherein each of said elongated shapes comprises a generally rectangular shape.

14. Apparatus according to claim 12 wherein each cutting edge defines a flat plane which is generally perpendicular to said central axis of said tube.

15. Apparatus according to claim 12 wherein each cutting edge defines a flat plane which is inclined with respect to said central axis of said tube.

16. Apparatus according to claim 12, wherein each cutting edge forms a curved plane which extends convexly outward of said distal end of said tube.

17. Apparatus according to claim 11 wherein each of said tubes further comprises at least one barb situated axially inward of its cutting edge and pointing axially inward with respect to said cutting edge and inclined inwardly from said wall of said tubular part.

18. A device according to claim 17 wherein said barb is pierced and bent out of the wall of said tubular part.

19. Apparatus according to claim 11 further comprising suction means for applying suction to the proximal end of each of said tubes.

* * * * *